United States Patent [19]

Brouillard et al.

[11] 4,304,857

[45] Dec. 8, 1981

[54] WHOLE CELL ENZYME COMPOSITION CONTAINING FUMED SILICA

[75] Inventors: Robert E. Brouillard; Hirschel A. Katz, both of Cedar Rapids; Howard L. Muenchow, Marion, all of Iowa

[73] Assignee: Penick & Ford, Limited, Cedar Rapids, Iowa

[21] Appl. No.: 113,554

[22] Filed: Jan. 21, 1980

[51] Int. Cl.³ .................... C12P 19/24; C12N 11/14
[52] U.S. Cl. ...................................... 435/94; 435/41; 435/176; 435/288; 435/830
[58] Field of Search ............... 435/176, 187, 188, 94, 435/41

[56] References Cited

U.S. PATENT DOCUMENTS

| | | | |
|---|---|---|---|
| 3,935,069 | 1/1976 | Long | 435/94 |
| 4,138,292 | 2/1979 | Chibata et al. | 435/176 |
| 4,144,127 | 3/1979 | Enokizono et al. | 435/176 |
| 4,153,510 | 5/1979 | Messing et al. | 435/176 |

Primary Examiner—Lionel M. Shapiro

[57] ABSTRACT

A dimensionally stable glucose isomerase composition having improved hydraulic characteristics and suitable for continuous column isomerization of glucose to fructose is produced by incorporating a low density, high surface area silica such as fumed silica into wet whole microorganism cells, and extruding and drying the cells to obtain the cells in particulate form suitable for continuous column use. This technique is also applicable to microorganism cells containing other enzymes.

20 Claims, 1 Drawing Figure

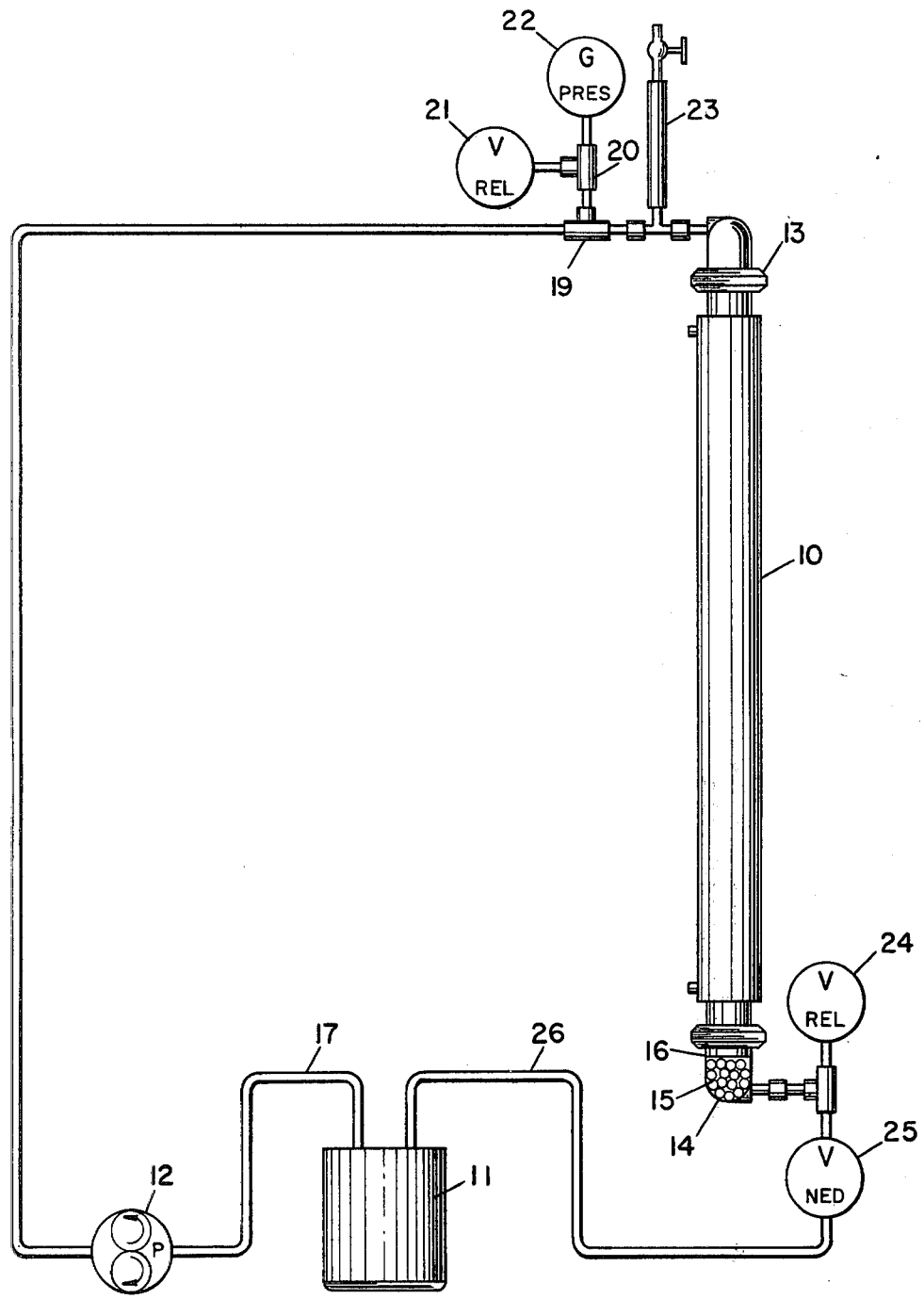

WHOLE CELL ENZYME COMPOSITION CONTAINING FUMED SILICA

BACKGROUND OF THE INVENTION

This invention relates to enzyme compositions comprising whole microorganism cells, to methods of making such compositions, and to methods for using such compositions to carry out enzymatic reactions. More particularly, this invention relates to an improved glucose isomerase enzyme composition comprising whole microbial cells, to methods of making such compositions, and to methods of using such compositions for isomerizing glucose to fructose.

U.S. Pat. Nos. 3,821,086 to Lee et. al., and 3,935,069 to Long, disclose processes for preparing flocculated whole enzyme-containing microorganism cells and for using such cells in continuous column operations to carry out enzymatic reactions. Preparation of whole flocculated Arthrobacter cells containing glucose isomerase and the use of such cells to isomerize glucose to fructose are among the processes disclosed. U.S. Pat. No. 4,060,456 to Long also discloses the preparation of whole flocculated Arthrobacter cells containing glucose isomerase and the use of such cells to isomerize glucose to fructose.

The use of whole flocculated enzyme-containing microorganism cells for carrying out enzymatic reactions represents a major improvement over the use of cell-free enzyme extracts. Flocculated whole cells can be used in continuous column reactions and can also be used repeatedly in batch reactions. Cell free extracts, on the other hand, are generally water soluble and therefore can be used only once and only in batch reactions. The use of flocculated whole cells also represents a significant improvement over the use of non-flocculated whole cells containing enzymes, as disclosed for example in U.S. Pat. No. 3,817,832 to Lloyd et. al., because flocculated cells can be used in continuous columns while non-flocculated cells are suitable for use only in shallow beds.

Although the use of flocculated whole microorganism cells represents an important step forward in enzyme technology, such cells are subject to compaction under high hydrostatic heads, so that the column height must be limited. U.S. Pat. No. 3,935,069 to Long, cited supra, describes the preparation and use of hardened flocculated microbial cell aggregates, in which magnesium oxide or other inorganic compound (i.e., an oxide, hydroxide, phosphate or sulfate of magnesium, calcium, iron or manganese) is added to a fermentation broth or cell susspension just prior to the addition of flocculants. Comparative test data show that the flow rate of glucose solution through magnesium oxide-hardened Arthrobacter cells occurs much more slowly than through non-hardened Arthrobacter cells under similar test conditions. The preparation and use of enzyme compositions comprising an enzyme attached to a support or carrier is also well known. Numerous references describe immobilized enzymes of this type. Carriers may be hard material such as porous glass or polystyrene beads, or materials affording a high void volume such as regenerated cellulouse (see U.S. Pat. No. 4,029,546 to Brouillard); immobilized enzymes on either type of carrier are suitable for continuous column operations. However, preparation of enzymes immobilized on a carrier requires extraction and purification of the enzyme to obtain a cell-free extract, followed by binding the enzyme to the carrier, usually with the aid of a binding agent. Whole cell enzyme compositions are more desirable, since they do not require these processing steps, provided the whole cell compositions are sufficiently hard for use in a column of substantial height.

SUMMARY OF THE INVENTION

Novel enzyme compositions in particulate form, comprising flocculated whole microoganism cells having an enzyme associated therewith, and containing an effective strength-imparting amount of fumed silica, are obtained according to this invention. These cell particles are prepared by adding an effective strength-impart amount of fumed silica to wet enzyme-containing microorganism cells which have not been previously dried, extruding the resulting mixture, and drying the extruded cells. An enzyme-catalyzed transformation of a substrate may be carried out according to this invention by contacting an aqueous solution of the substrate with particles of the aforesaid enzyme composition.

DRAWING

The sole FIGURE of drawing is a schematic diagram illustrating an apparatus for testing the hydraulic properties of whole cell enzyme compositions.

DETAILED DESCRIPTION

According to a preferred embodiment of this invention, flocculated whole cells of a glucose isomerase-producing strain of the microorganism Arthrobacter are treated with from about 2 to about 40% by weight of fumed silica, based on dry cell weight, and the resulting cell mass is extruded, dried, ground and sieved to produce dried aggregate particles of desired size.

Although the preferred microorganism cells are glucose isomerase-containing microorganism cells of the genus Arthrobacter, the invention is also applicable to glucose isomerase-containing cells derived from other Arthrobacter strains, and from other genera of microorganisms. The invention is also applicable to enzyme-containing microorganism cells having enzyme activities other than glucose isomerase activity.

The most preferred strain of Arthrobacter for the purpose of this invention is NRRL B-3728. Another desirable Arthrobacter strain is NRRL B-3726. Cells of the selected Arthrobacter strain are cultivated in a sterile medium containing sources of carbohydrate, nitrogen, and inorganic salts, as described in U.S. Pat. No. 3,645,848. Arthorbacter microorganisms are preferred over other glucose isomerase-containing microorganisms because the glucose isomerase activity in Arthrobacter microorganisms is inherently fixed or stabilized within the cells, so that no treatment is necessary in order to stabilize the glucose isomerase activity, which is required for long term continuous or repeated use of the cells.

Other glucose isomerase producing microorganisms, such as Streptomyces, *Bacillus coagulans* and *Actinoplanes missouriensis* can be used in place of Arthrobacter if desired, provided they are treated prior to use to stabilize their glucose isomerase activity. These microorganisms may be cultivated according to methods known in the art. Other microorganisms in which an enzyme is produced intracellularly may also be processed and used according to this invention.

Microorganism cells masses which are treated according to this invention are principally in the form of whole cells. Some cell disruption occurs in processing according to this invention, and this is not detrimental. However, rupturing of a major portion of the microorganism cells is not contemplated.

After fermentation the cells formed in the broth are flocculated with a polyelectrolyte or combination of polyelectrolytes, preferably an anionic electrolyte and a cationic electrolyte. When a combination of cationic and anionic electrolytes is used, it is preferred to add the cationic electrolyte first. The preferred polyelectrolytes are "Primafloc C-7" (cationic) and "Primafloc A-10" (anionic) broth made by Rohm and Haas Co. Philadelphia, Pa. Others which may be used are: "Catfloc," made by Calgon Corp., Pittsburgh, PA; "Delfloc 763," made by Hercules Inc., Wilmington, DE; "Dow XD-1923," made by Dow Chemical Co., Midland MI; and "Natron 86," made by National Starch and Chemical Corp, Plainfield, N.J. Suitable amounts and further flocculation details are given in U.S. Pat. No. 4,060,456.

The flocculated cell mass is preferably frozen and then thawed in warm water. it is not necessary that the cell mass be frozen. Freezing is preferred, however, because freezing preserves the cells from microbiological spoilage and makes it possible to hold the cells for extended periods before further processing.

The thawed cells are filtered and compressed to reduce the moisture level.

Amorphous silica, preferably synthetic fumed silica, is added to the wet cell mass in amount ranging from about 2 to about 40% by weight, based on the total enzyme composition weight (dry basis). Amounts from about 5% to about 20% by weight are preferred. Amounts less than 2% are generally insufficient to achieve any marked improvement in hydraulic properties over those obtained in the absence of silica, and amounts larger than about 20% do not result in further improvement in particle hardness. If excessive amounts of silica are used, particle integrity may be diminished.

The preferred silica for this invention is synthetic fumed silica. In the usual method of manufacture, oxygen is passed through silicon tetrachloride and the resulting mixture is fed with natural gas into a burner. Hydrolysis takes place in the resulting flame, producing vitreous silica. The resulting product is amorphous, very pure, of very low density, has a surface area of at least about 50 square meters per gram (typically 50–400 square meters per gram) and a very small amount of chemically bound water and is very inert. Typical properties of fumed silica are reported in Kirk-Othmer "Encyclopedia of Chemical Technology," 2nd ed, 1969, vol. 18, page 67.

Other forms of amorphous silica, having high surface areas (above about 50 square meters per gram) can be used, but do not give as good results as fumed silica.

After addition of fumed silica, the cell mass is extruded, dried, ground and sieved to desired particle size, usually from 10–30 mesh (U.S. Bureau of Standards), preferably from 16 to 20 mesh. Suitable procedures are more fully disclosed in U.S. Pat. No. 4,060,456.

The synthetic fumed silica can be added at other points in the process, provided the cell mass is wet and has not been previously dried. Thus, fumed silica may be added to the fermentation broth before flocculation. Alternatively, fumed silica may be added between the cationic and anionic polyelectrolytes. It is ordinarily preferred to add the fumed silica prior to extrusion. In fact, the fumed silica appears to facilitate smoother flow during extrusion.

Silica can be used in combination with other materials to increase the hardness of the enzyme particles while maintaining high activity levels. A particularly desirable product comprises Arthrobacter cells containing 5% fumed silica and 2% magnesium oxide, both by weight based on total enzyme composition weight (dry basis). However, much heavier additive loadings, for example 40% fumed silica and 5% magnesium sulfate, both by weight based on total enzyme composition weight (dry basis), can be used. The presence of magnesium sulfate in this combination appears to result in smoother flow during extrusion than that obtainable with 40% by weight of fumed silica as the sole additive. Other combination products include silica-containing cells treated with glutaraldyhyde or with resin, for example as illustrated in Example 5 and 4 respectively. Total additive loadings up to 45% of enzyme composition weight (dry basis) have been demonstrated not to impair particle integrity to any appreciable extent, and it appears that higher additive loadings, up to about 50% or more of total particle weight (dry basis) can be used.

The dried cells may be conditioned prior to use by treatment with an aqueous glucose solution containing a small amount of a magnesium salt. Aqueous glucose solutions used for conditioning may have the same compositions as those used for glucose isomerization. Alternatively, the dried cell particles may be conditioned prior to use by treating with an aqueous solution of sodium bicarbonate and a magnesium salt, as more fully described in U.S. Pat. No. 4,060,456. The wet conditioned cells may be loaded into a column as described in U.S. Pat. No. 4,060,456.

When a glucose isomerase enzyme composition according to this invention is prepared from a microorganism from a genus other than Arthrobacter, it is usually necessary to treat the microorganism prior to use in order to stabilize the glucose isomerase activity. For example, Streptomyces organisms can be stabilized by heat treatment at 60° C. as disclosed in "Fermentation Advances" cited supra.

In a preferred glucose isomerization process according to this invention, syrup (an aqueous glucose solution containing about 50% by weight of glucose on the dry basis and having a magnesium ion concentration of 0.004 M) is introduced down flow through the column at 60° C. to effect isomerization. The column is preferably jacketed to maintain the temperature of 60° throughout. The product, which is continuously obtained at the bottom of the column contains about 42% by weight of fructose on the dry basis. The product can be purified by means known in the art, as for by example treatment with anion and cation exchange resins and with decolorizing carbon. More broadly, the glucose concentration may range from about 30% to about 60% (or slightly higher) by weight and the isomerization temperature may be in the range of about 50° to about 70° C., as is known in the art.

Enzyme-catalyzed substrate transformations other than isomerization of glucose to fructose can be carried out by contacting an aqueous solution of the substrate with silica-containing whole flocculated microorganism cells prepared according to this invention and having the desired enzyme activity. Suitable art-recognized conversion conditions may be used.

This invention provides many important advantages, as follows:

A major advantage is that microorganism particles of this invention can be used in fixed bed columns of substantially greater height than has been possible heretofore with whole cell enzymes.

Another advantage is that compaction of the cell bed is minimized.

Another advantage is the channeling of the enzyme bed is minimized.

Another advantage is that flow of substrate solution through the enzyme bed is substantially unimpeded, resulting in very little back pressure through the bed.

Another advantage is that swelling of enzyme during hydration (conditioning) is minimized.

Another advantage is that treatment according to the present invention results in high rate of substrate transformation and fructose production in particular, in a fixed bed column operation.

This invention will now be described further with reference to specific embodiments thereof.

Column Performance Evaluation Procedure

The following laboratory test procedure was developed to evaluate the hydraulic characteristics of enzyme compositions prepared according to this invention.

Referring now to the sole FIGURE of drawing, the test apparatus includes a jacketed glass column 10 for the enzyme, a water reservoir 11 shown as a beaker, a gear pump 12, and flexible tubing forming a closed loop connecting these elements. At the top of the column 10 is an inlet header 13. At the bottom of the column is an outlet header 14, similar in structure to the inlet header 13. The outlet header 14 contains a bed of rocks 15 and a 16 mesh stainless steel screen 16 on top of the bed of rocks. A wad of medium grade glass grade wool rests on top of the screen.

The test apparatus includes a flexible tube 17 extending from reservoir 11 below the water line to the inlet of pump 12, and a flexible tube 18 connected to the outlet of pump 12. The downstream end of tube 18 is connected to a T junction 19. One port of this T junction is connected to a second T junction 20, to which a relief valve 21 and pressure gauge 22 are connected. An air vent 23, placed between T junction 19 and inlet 13 of column 10, and connected to the third port of T junction 19, permits manual venting of air prior to the beginning of a test. The height of column 10, exclusive of the headers 13 and 14 at either end, is about 38 inches.

A pressure gauge 24 and a needle valve 25 are mounted in the line at the bottom of column 10. A flexible hose line 26 connects the outlet side of 25 with beaker 11, and provides for return of water to the reservoir.

The difference in readings between upstream pressure gauge 22 and downstream pressure gauge 24 indicates the pressure drop through column 10.

The operating procedure is as follows: The column is loaded with enzyme which has been swollen and degassed in deionized water. Suficient enzyme is used to essentially fill the colum 10 (about 38-inch bed depth). The top of the column is installed and the pump 12 run at low speed to fill the system with water, being careful to vent it of all air. The enzyme bed depth is measured and recorded.

The test is run with the valve 25 at the bottom of the column fully open. Severe, above normal water flow using a column of this size for producing a 42% dry solids fructose syrup is about 0.6 gallon per hour. For these tests, the water flow rate will run as high as 70 gallons per hour.

The unit is initially operated for a 20-minute period at 2 psig back pressure (pressure at top of column). The stabilizd flow rate for the period is obtained. Depending on the physical nature of the enzyme sample, this flow rate will range from about 15 to 40 gallons per hour (gph).

The pump 12 is then speeded up to develop a maximum back pressure of 28 psig. This pressure is controlled for a period of 1.5 hours through reduction of the flow rate which becomes necessary as enzyme compaction progresses. The relief valve 21 (set to open at 28 psig) also serves to maintain this pressure. In cases where resistance through the enzyme bed is very low (when little compaction occurs, a back pressure of 28 psig is never attained, even at the maximum pump speed. In such cases, the pump is run at its maximum speed for the 1.5 hours compaction period. Throughout this period, flow rates, pressure drop through the column, and enzyme bed depth measurements are recorded. Drop in flow rate, increase in pressure drop through the column, and decrease in bed depth all indicate enzyme compaction.

The speed of the pump is then reduced so that a 2 psig back pressure is once more obtained and the water flow rate again measured. The percent reduction in flow rate (from the flow rate obtained during the initial 20-minute compaction period at 2 psig back pressure) is another indication of the degree of enzyme compaction and performance.

The critical factors determining enzyme performance in columns are:

A. Flow rate (gph) through test material during initial 2 psig back pressure period, compared to flow rate without test material (40 gph).
B. Flow rate (gph) through test material during high flow period compared to flow rate without test material (71 gph).
C. Flow rate (gph) through test material during final 2 psig back pressure period, compared to flow rate without test material (40 gph).
D. Percent flow rate drop between initial 2 psig operation and final 2 psig operation (after high flow period).
E. Maximum back pressure during high flow.
F. Maximum pressure drop during high flow.

The criteria used to evaluate hydraulic performance are given in Table I below.

TABLE I

| Evaluation of Hydraulic Performance | | | |
|---|---|---|---|
| | 1 | 2 | 3 |
| A. Flow rate initial 2 psig (gph) | 30–40 | 20–30 | 10–20 |
| B. Flow rate initial, high flow (gph) | 60–71 | 40–60 | 20–40 |
| C. Flow rate final 2 psig (gph) | 30–40 | 20–30 | 10–20 |
| D. Percent flow rate drop 2 psig (%) | 0–20 | 20–40 | 40+ |
| E. Maximum back pressure (psig) | 0–15 | 15–20 | 20–28 |
| F. Maximum pressure drop (psig) | 1–5 | 5–10 | 10+ |

The products of this invention are excellent in hydraulic performance, while those in the prior art are usually poor and never better than fair.

Colum 1—Excellent
Column 2—Good-Fair
Column 3—Poor

This invention will now be described with respect to the following examples. All quantities are given in percentage by weight, based on total composition weight (including additives where present) on the dry basis. The fumed silica used in the examples was "Cab-O-Sil" grade MS-7, having a surface area of about 200 m$^2$/g. and made by Cabot Corporation, Cambridge, Mass.

EXAMPLES

EXAMPLE 1

The cultivation of Arthrobacter nov. sp. NRRL B-3728 was carried out as described in U.S. Pat. No. 3,645,848 to give 400 gallons of culture broth having a pH of 5.7. This broth was gently agitated and to it were added 53.3 gallons of a 1.5% solution of "Primafloc C-7" (previously adjusted to pH 5.0) followed immediately with 53.3 gallons of a solution of "Primafloc A-10." Addition of the flocculating agents was effected over a period of about 15 minutes and flocculation of the cells was essentially complete within 20 minutes. Filtration yielded 125 pounds of wet, flocculated cells having a moisture content of approximately 80%. The cells were frozen at −5° C. and stored for two weeks. The frozen blocks were then thawed in water. The wet floc was then isolated by filtration and compressed to remove excess water, and 5% by weight of fumed silica ("Cab-O-Sil"), was blended into the floc. This wet floc was then extruded through a die with 1.5 mm diam. holes using Model EXDCS-100 extruder supplied by Elanco Extruder Products Company of Indianapolis, Ind. The extruded floc was subsequently dried at 55°–60° C. by means of a fluidized bed dryer (Type TF-30 Glatt Dryer available from Artisian Industries of Waltham, Mass. 02154), giving 30 pounds of dried material having a moisture content of slightly less than 10%.

The dried, flocculated cell material was milled and sieved to give particles in the 16–20 mesh range (U.S. Bureau of Standards). A 3-gram portion of the 16–20 mesh material was suspended in an aqueous solution that was 0.05 molar with respect to sodium bicarbonate and 0.01 molar with respect to magnesium chloride. After the particles had swelled to the maximum extent, they were packed into a 1-inch diameter glass column and the floc particles were washed by passing additional quantities of the sodium bicarbonate-magnesium chloride solution through the packed bed equivalent to approximately three times the volume occupied by the packed bed. The packed column was heated to 60° C. and a 2.0 M dextrose solution containing 0.004 M magnesium chloride (previously adjusted to pH 8.5 with sodium hydroxide) was passed through the column at a flow rate sufficient to give 42% fructose in the effluent. After two days of operation, the column was producing at the rate of 95 grams of product per gram of enzyme per day and after 25 days it had produced over 2000 grams of product. There was no evidence of back pressure in the column at any time.

EXAMPLE 2

Example 1 was repeated without freezing the floc with essentially the same results.

EXAMPLE 3

Two samples of immobilized enzyme were prepared as in Example 1 except that sample 1 did not contain fumed silica and sample 2 contained 10% by weight of fumed silica (based on dry cell weight) blended into the floc. This material was extruded through a die containing 1.5 mm diameter holes, dried and sieved.

The dry finished product was subjected to hydraulic testing. The "Cab-O-Sil" containing sample exhibited excellent hydraulic characteristics whereas the sample without "Cab-O-Sil" did not perform as well. Results are given in Table II.

TABLE II

| Sample | Flow rate, gph | | |
|---|---|---|---|
|  | A | B | C |
| 1 0% "Cab-O-Sil" | 37.6 | 43.1 | 16.7 |
| 2 10% "Cab-O-Sil" | 37.6 | 72.1 | 36.7 |

In the above Table II, A, B, and C have the same significance as in the "Column Performance Evaluation Procedure" described supra.

EXAMPLE 4

Frozen flocculated cells which had been prepared as described in Example 1 were thawed in water. The wet floc was filtered, compressed to reduce the moisture level and divided into three parts. Part 1 was processed without additives to a 16–20 mesh dried product according to the procedure in Example 1. Part 2 was blended with 5% "Beetle 55" (a methylated urea-formaldehyde resin, American Cyanamid Company) containing an acid catalyst No. 600 (American Cyanamid Company) and processed to a 16–20 mesh dried product according to the procedure in Example 1. Part 3 was blended with 5% "Beetle 55" containing an acid catalyst No. 600 and 5% "Cab-O-Sil," and the blend was processed to a 16–20 mesh dried product according to the procedure in Example 1. The three products were assayed for glucose isomerase activity with the following results:

TABLE III

| Part | Activity Units/g | Hydraulic Performance |
|---|---|---|
| 1 | 85 × 10$^{-3}$ | Fair |
| 2 | 59 × 10$^{-3}$ | Excellent |
| 3 | 81 × 10$^{-3}$ | Excellent |

EXAMPLE 5

A fermentation beer containing Streptomyces olivaceus NRRL 3583 bacterial cells was obtained by culturing such cells in a xylose-containing medium in a known manner. The fermentor beer was then adjusted to a pH of 8.2 by addition of sodium hydroxide. A 1% (weight/volume basis) aqueous solution of glutaraldehyde was added to the fermentor beer in an amount of 7 weight percent glutaraldehyde based on the dry weight of the cells in the beer. The resulting mixture was stirred for 1½ hours during which time sodium hydroxide was added to maintain the pH at 8.2. The cells were then filtered, washed at pH 8 and then dried at 60°–70° C. to a moisture content of 3–10 weight percent. This dried filter cake of agglomerated cells was then broken, and the broken pieces were collected on sieves to obtain a fraction that was retained on a 60 mesh screen and which passed through a 20 mesh screen.

The activity of the product was 50×10$^{-3}$ units of glucose isomerase per gram d.b. where one unit is defined as the amount of enzyme which catalyzes the formation of 1 gram of fructose per minute under the following conditions: 60° C., 1.67 molar glucose, pH 7.75 and 0.4 molar magnesium added as magnesium chloride.

When an identical reaction was run using 10% by weight of fumed silica added during the glutaraldehyde treatment the activity was $62 \times 10^{-3}$ units per gram.

EXAMPLE 6

The cultivation of *Streptomyces olivochromogenes* was carried out as described in U.S. Pat. No. 3,622,463. The mycelia were harvested by centrifugation and washed. A 200 gram portion of the wet mycelia was resuspended in 4 liters of water and treated sequentially with 300 milliliters of a 1.5% solution of "Primafloc C-7" (previously adjusted to pH 8.0) and 100 milliliters of a 1.5% solution of "Primafloc A-10" (previously adjusted to pH 8.0). Gentle agitation was continued for a few minutes before recovering the flocculated mycelia by vacuum filtration. The wet, flocculated mycelia were blended with 5% by weight of fumed silica and dried in an oven for 18 hours at 56° C. to yield 40 grams of dry material. This dry floc was crushed and sieved to obtain particles of 16–20 mesh size (U.S. Bureau of Standards). A 4-gram portion of the dry, 16–20 mesh material was suspended in an aqueous solution that was 0.05 molar with respect to sodium bicarbonate and 0.01 molar with respect to magnesium chloride. After the particles had swelled to the maximum extent, they were packed into a 1-inch diameter glass column and the floc particles were washed by passing 4 liters of additional sodium bicarbonate-magnesium chloride solution through the packed bed over a 2 hour period. The packed column was heated to 60° C. and a 2.0 M dextrose solution at pH 8.2 containing 0.004 M magnesium chloride was passed through the column at a rate to give 42% fructose in the effluent. After 4 day of operation the column was producing at a rate of 85 grams of product per gram of enzyme per day. A similar experiment without fumed silica the same conditions gave 60 grams.

EXAMPLE 7

Glucose isomerase containing cells of *Bacillus coagulans* NRRL 5656 were recovered from the fermentation broth by centrifugation and the pH adjusted to 6.3. The cells were partially disrupted in the process.

The cells containing approximately 90% water were treated for one hour with a 10% solution of glutaraldehyde containing 10% by weight of fumed silica on the dry weight of the cells. The coherent mass formed was washed with water and filtered. The resulting cake was dried at 50° C., ground and sieved. The 16–20 mesh fraction gave an activity of $53 \times 10^{-3}$ units per grams.

The the experiment was repeated without fumed silica; the activity was $44 \times 10^{-3}$ units per gram.

EXAMPLE 8

Dried flocculated cells of Arthrobacter nov. sp. NRRL B-3728 containing 5% by weight of fumed silica ("Cab-O-Sil") and 2% by weight of powdered magnesium oxide (magnesia), both based on total dry enzyme composition weight (i.e., dry cell weight plus additive weight) were prepared, except for quantities of additives and extrusion die diameter, by the method of Example 1. The extrusion die had a diameter of 3/64 inch (1.2 mm). The resulting dry pellets were predominantly (92%) 18–20 mesh. (All particles were −14+30 mesh. Mesh analysis also showed 5.5% 16–18 mesh and 2% 20–25 mesh). The bulk density was 46.76 lb/ft³, and hardness and attrition resistance were good.

The dried particles were loaded into a column and swelled in glucose syrup having a pH of 7.7. The swelling ratio was 2.8. The swelling ratio is the settled volume of swelled pellets divided by the dry volume. This means that 100 cc of dry pellets after swelling would occupy 280 cc.

EXAMPLE 9

Dried flocculated cells of Arthrobacter nov. sp. NRRL B-3728, containing 40% by weight of fumed silica ("Cab-O-Sil") and 5% by weight of magnesium sulfate, both based on total dry weight, were prepared (except for additive quantities, extrusion die diameter, and pH adjustment) as described in Example 1. The die diameter was 1/32 inch (0.8 mm). The thawed floc slurry was adjusted to pH 8 with soda ash (sodium carbonate). The resulting dried cells were in the form of rods predominantly (86%) 20–25 mesh. The bulk density was 40.79 lb/ft³, hardness was excellent, and attrition resistance was satisfactory.

The dried particles were loaded into a column and swelled with glucose syrup (pH 5.8) as described in Example 1. Glucose syrup was then passed through the column as described in Example 1. The initial production rate was 75 grams of product per gram of enzyme per day. Total quantities of product were 538 grams of product per gram of enzyme composition (including additives, dry basis) after 10 days, and 1264 grams of product per gram of enzyme composition after 25 days. On the diluent-free basis, the corresponding quantities were 978 grams of product per gram of cells (dry basis) after 10 days, and 2298 grams of product per gram of cells (dry basis) after 25 days. These data are also shown in Table IV, which follows Examples 11 and 12, for comparison purposes.

EXAMPLES 10 and 11

Dry flocculated cells of Arthrobacter nov. sp. NRRL B-3728, containing 7% and 15%, respectively, of fumed silica ("Cab-O-Sil"), were prepared according to the method of Example 1, except that: (1) silica quantities were as stated in these examples, (2) the extrusion die diameter was 1/32 inch (0.8 mm), and (3) the thawed floc slurry was adjusted to pH 8 with soda ash. Amounts are based on the total dry weight of the enzyme composition. The dried pellets in each case were in the form of rods predominately (about 88–90%) in the 20–30 mesh size range. Bulk densities were 41.98 and 36.49 lb/ft³, respectively. Both products had excellent attrition resistance and good to very good hardness. The dried enzyme preparations contained 7.1% and 7.3% by weight of water, respectively.

The enzyme preparations were loaded into columns after swelling in 45% dry basis glucose syrup. This syrup was obtained by dissolving "Staleydex" (99% glucose solids) in distilled water. After swelling, the supernatant syrup exhibited a pH of 6.2. Glucose syrup, 45% by weight glucose and 0.002% by weight MgSO₄ was then passed through each column as described in Example 1. The initial production rates were 95 and 83 gm. product/gm enzyme/day, respectively. Total quantities of product per gram of enzyme pellets, on both the dry cell weight (i.e., additive-free and moisture-free) and the total dry composition (i.e., including additives but excluding moisture) bases, are given in Table IV below. Data from Example 9 are also included for comparison.

TABLE IV

| Example | 10 | 11 | 9 |
|---|---|---|---|
| Additive: | | | |
| Fumed silica | 7 | 15 | 40 |
| Magnesium sulfate | — | — | 5 |
| Lb product/lb enzyme (including additives) | | | |
| After 10 days | 761 | 699 | 538 |
| After 25 days | 1774 | 1654 | 1264 |
| Lb product/lb dry cells | 818 | 822 | 978 |
| (additive free) | 1908 | 1940 | 2298 |

The productivities (i.e., pounds of product on the dry basis per pound of enzyme pellets) of enzyme compositions described in this specification are fairly similar, regardless of percentage of additive present, when enzyme weight is given on the additive-free basis, as comparison of Example 9, 10 and 11 shows. Compositions containing large amounts of additives, such as the composition described in Example 9, have lower productivities than less heavily loaded compositions on the basis of either actual or total dry basis composition weight.

What is claimed is:

1. A process for preparing a column material comprising enzyme-containing microorganism cell particles of improved strength, which process comprises blending an effective strength-improving amount of fumed silica into flocculated wet enzyme-containing whole microorganism cells which have not been previously dried, extruding the resulting mixture and drying the extruded cells.

2. A process according to claim 1 in which said fumed silica has a surface area of at least about 50 square meters per gram.

3. A process according to claim 1 in which the amount of fumed silica is from about 2% to about 40% by weight, based on the dry cell weight.

4. A process according to claim 1 in which the amount of fumed silica is from about 5% to about 20% by weight, based on the dry cell weight.

5. A process according to claim 1 in which the microorganism is a glucose isomerase-containing microorganism.

6. A process according to claim 1 in which the microorganism is of the genus Arthrobacter.

7. A process according to claim 1 in which the wet cells are extruded into pellets after addition of silica and before drying.

8. A process according to claim 1 in which the glutaraldehyde is also added to said cells prior to drying.

9. An enzyme composition in particulate form for use in a column comprising flocculated whole microorganism cells having an enzyme associated therewith, said cells containing an effective strength-imparting amount of fumed silica.

10. An enzyme composition according to claim 9 in which said fumed silica has a surface area of at least about 50 square meters per gram.

11. An enzyme composition according to claim 9 in which the amount of fumed silica is from about 2% to about 40% by weight, based on the dry cell weight.

12. An enzyme composition according to claim 9 in which the amount of fumed silica is from about 5% to about 20% by weight, based on dry cell weight.

13. An enzyme composition according to claim 9 in which said microorganism cells contain glucose isomerase.

14. An enzyme composition according to claim 13 in which said microorganism cells are of the genus Arthrobacter.

15. A process for carrying out an enzyme-catalyzed transformation of a substrate which comprises contacting an aqueous solution of said substrate with particles of an enzyme composition comprising a column bed of flocculated whole microorganism cells having an enzyme associated therewith, said cells containing an effective strength-imparting amount of fumed silica.

16. A process according to claim 15 in which said fumed silica has a surface area of at least about 50 square meters per gram.

17. A process according to claim 15 in which the amount of fumed silica is from about 2% to about 40% by weight, based on dry cell weight.

18. A process according to claim 15 in which the amount of fumed silica is from about 5% to about 20% by weight, based on dry cell weight.

19. A process according to claim 15 in which said solution is passed through a fixed bed of particles of said enzyme composition.

20. A process for isomerizing glucose to fructose according to claim 15 in which said substrate is glucose and said cells have glucose isomerase associated therewith.

* * * * *